(12) United States Patent
Gonzalez et al.

(10) Patent No.: US 9,180,287 B2
(45) Date of Patent: Nov. 10, 2015

(54) USE OF LOCAL ANESTHESIA AND ELECTRICAL STIMULATION IN PERIPHERAL WOUND TREATMENT

(71) Applicant: Diabetic Neuropathy Network, Inc., San Antonio, TX (US)

(72) Inventors: Victor M. Gonzalez, San Antonio, TX (US); Francisco J. Gonzalez, El Paso, TX (US)

( * ) Notice: Subject to any disclaimer, the term of this patent is extended or adjusted under 35 U.S.C. 154(b) by 111 days.

(21) Appl. No.: 14/157,822

(22) Filed: Jan. 17, 2014

(65) Prior Publication Data

US 2014/0207050 A1    Jul. 24, 2014

Related U.S. Application Data

(60) Provisional application No. 61/754,226, filed on Jan. 18, 2013.

(51) Int. Cl.
| | |
|---|---|
| *A61N 1/30* | (2006.01) |
| *A61N 1/04* | (2006.01) |
| *A61M 19/00* | (2006.01) |
| *A61N 1/36* | (2006.01) |
| *A61N 1/32* | (2006.01) |
| *A61M 21/00* | (2006.01) |

(52) U.S. Cl.
CPC ............ *A61N 1/0452* (2013.01); *A61M 19/00* (2013.01); *A61N 1/0468* (2013.01); *A61N 1/36003* (2013.01); *A61N 1/36014* (2013.01); *A61M 2021/0072* (2013.01); *A61M 2210/086* (2013.01); *A61N 1/326* (2013.01); *A61N 1/36021* (2013.01)

(58) Field of Classification Search
CPC ................... A61M 19/00; A61M 2021/0072; A61M 2210/086; A61M 21/00; A61M 2021/0005; A61M 2210/00; A61M 1/0452; A61M 1/0468; A61M 1/326; A61M 1/36003; A61M 1/36014; A61M 1/36021; A61M 1/00; A61M 1/02; A61M 1/04; A61M 1/0404; A61M 1/0408; A61M 1/00456; A61M 1/18; A61M 1/32; A61M 1/36
USPC .......................................................... 604/21
See application file for complete search history.

(56) References Cited

U.S. PATENT DOCUMENTS

2004/0267189 A1\* 12/2004 Mavor et al. .................... 604/20
2008/0287856 A1\* 11/2008 MacDonald et al. ........... 604/20
2011/0093033 A1\*  4/2011 Nekhendzy .................... 607/46

\* cited by examiner

*Primary Examiner* — Jason Flick
(74) *Attorney, Agent, or Firm* — Jackson Walker L.L.P.

(57) ABSTRACT

A wound therapy method that results in improved wound healing for conditions including diabetic foot ulcers, pressure ulcers, and arterial and venous ulcers is described. The wound therapy method uses local anesthetic injections in an area surrounding the wound combined with electrical stimulation causing local and deep muscle contraction in the same area. The method leads to increased vasodilation, increased tissue oxygen levels at the target site, and increased blood flow to the target site. This causes local angiogenesis and tissue perfusion that increases wound healing rates and decreases future wound occurrences.

7 Claims, 4 Drawing Sheets

(a)

(b)

(a)

(b)

(a)

(b)

USE OF LOCAL ANESTHESIA AND ELECTRICAL STIMULATION IN PERIPHERAL WOUND TREATMENT

BACKGROUND

This application claims the benefit of U.S. Provisional Patent Application Ser. No. 61/754,226, entitled USE OF LOCAL ANESTHESIA AND ELECTRICAL STIMULATION IN PERIPHERAL WOUND TREATMENT, filed on Jan. 18, 2013, the entire content of which is hereby incorporated by reference.

The present disclosure pertains to methods for treating wounds, improving wound healing, treating peripheral neuropathic pain, and regeneration of sensation caused by peripheral nerve damage, by administering a combination of local and deep nerve analgesia and electrical stimulation.

Slow healing wounds and chronic foot ulcers are a common problem in the United States and can dramatically affect the quality of life of patients who present with this. Patients with Diabetes and peripheral arterial disease are at risk for developing serious health problems that affect the eyes, kidney, skin, feet and heart. Foot ulcerations are one of the most common complications in patients with these conditions. The development of foot ulcers typically develop from diabetic neuropathy and large vessel disease such as patients who suffer from peripheral arterial disease. Most commonly diabetic foot ulcers ("DFUs") are caused by peripheral neuropathy complicated by deformity, callus, and trauma. Vascular insufficiency, infection, and failure to implement effective treatment of DFUs are linked to secondary medical complications, such as osteomyelitis and amputation. Approximately 15% of DFUs result in lower-extremity amputation. More than 85% of lower-extremity amputations in patients with diabetes occur in people who have had an antecedent foot ulcer.

The 5-year mortality rate for patients with neuropathic and ischemic DFUs is 45% and 55%, respectively. General healing rates for neuropathic DFUs have been reported in the literature. The meta-analysis of 10 control groups from clinical trials, using good standard wound care (including debridement and off-loading, and either saline moistened gauze or placebo gel and gauze) demonstrated that the weighted mean rates of neuropathic ulcer healing were 24.2% (95% confidence interval [CI] 19.5-28.8%) over 12-weeks and 30.9% (95% CI 26.6-35.1%) over 20 weeks. These data provide clinicians with a realistic benchmark for the rate of healing of neuropathic ulcers over 20 weeks.

SUMMARY

The present disclosure pertains to an approach to the treatment of peripheral wounds using a local anesthetic injected a various sites to promote vasodilatation and increased tissue oxygen levels at the target site, with combined electrical stimulation causing local and deep muscle contraction to promote increased blood flow to the targeted area. This combination causes local angiogenesis and tissue perfusion, thereby increasing wound healing rates and decreasing future wound occurrences due to long lasting effects of neuropathy and peripheral vascular disease.

Patients with various complications related to diabetes, peripheral vascular disease and chronic slow healing wounds have been treated using the present method. These patients had received appropriate medical therapy for their conditions. The procedure was developed for the control of pain that was manifest in these conditions. In the wound therapy method, a local injection of bupivacaine hydrochloride (such as Marcaine, Cook-Waite, Carestream Dental, Atlanta, Ga.) is injected at the surrounding site for improvement in local and systemic circulation as well as local vasodilatation and increased tissue perfusion and oxygenation. A peripheral nerve block is performed for improvement in tissue and nerve regeneration thereby reducing pain caused by peripheral neuropathy and promoting lasting benefits including decreased neuropathic pain and increased fine touch and proprioception. Electrical stimulation is then applied on each visit with ensuing deep muscle contraction in otherwise sedentary patients. All of the patients treated with this procedure reported significant improvement in regards to pain, edema, circulation, walking distance, and quality of life. Also reported was decreased need for neuropathic pain medications. When patients were treated only with electrical stimulation, there was no difference in wound healing or pain scale compared to no treatment at all. These patients either dropped out of the treatment or crossed over to the present wound therapy method.

The wound therapy method improves circulation through sympathetic and parasympathetic efforts, reduces overall polypharmacy, potentiates nerve regrowth, improves the overall quality of life, and is minimally invasive.

DETAILED DESCRIPTION OF PREFERRED EMBODIMENTS

Figure 1:
FIG. 1 shows photographs of a patient taken (a) at the early stages of treatment and (b) after further treatment, showing visibly healed skin.
Figure 1:

The wound therapy method of the present disclosure involves a combination of injections of anesthetic and electrical stimulation.

In particular, a solution of 0.25% bupivacaine hydrochloride is prepared and injected in amounts ranging from about 1 cc to about 2 cc at a plurality of nerve locations in proximity to the wound being treated. As an example, when the wound is in close proximity to the Mortise Joint, 2 cc of the solution is injected in the deep Peroneal nerve. Then the superficial Peroneal nerve is injected with 1.5 cc solution, the Saphenous nerve is injected with 1.5 cc solution, the Sural nerve is injected with 1.5 cc solution, and the Posterior Tibial nerve is injected with 2cc solution, in a like manner. Another example would be the treatment of a wound occurring along the inner thigh. The wound therapy method remains the same save the exception of the injection locations, which in this case would be the closest neurovasculature branch both distal and proximal to the wound margins with the number of injections determined by local anatomy. In this case the preferable nerves injected would be the Ilioinguinal nerve, Genitofemoral nerve, Obturator nerve, and most obvious the Anterior Cutaneous Femoral nerve. Electrostimulation therapy is then performed by placing contact pads in four locations in proximity to the wound. Electrostimulation is applied for about 15 minutes via an alternating current neuromuscular electrostimulation device delivering a high voltage (about a maximum of 440 V) and very low amperage (about 0.1 to about 4.4 milliamps). The stimulator uses a biphasic pyramidal wave with a frequency of about 47 Hz. Duty cycles may be fixed at about 1.5 seconds on and 1.8 seconds off. There is no ramp time. The intensity is the only variable. The intensity is controlled via a dial that is turned clockwise to increase intensity and counterclockwise to decrease intensity. The dial also has an off position at the its most extreme counterclockwise position. When the dial is turned in the clockwise direction it may be positioned anywhere along an incremental gradient beginning from zero and increasing to a maximum of one hundred at the farthest clockwise position. The intensity is determined by the patient's tolerance to the stimulation and at the minimum must produce involuntary muscle contraction. The therapy is repeated based on patient need and resolution of the wound.

Muscle contractions are generally stimulated with voltage and as a general rule the higher the amperage the greater the patient discomfort. In fact, most patients can only tolerate around 30 milliamps from a direct current device although these devices are capable of delivering around 90 milliamps at a maximum output of 125 volt. Therefore, an alternating current can achieve much higher voltage and correspondingly much lower amperage creating a distinct therapeutic benefit over direct current devices.

The wound therapy method is shown to lead to an increase in wound healing caused by multiple conditions including but not limited to diabetic foot ulcers, pressure ulcers, arterial, and venous ulcers. The wound therapy method also improves peripheral neuropathy and related syndromes, peripheral vascular disease, chronic lymphedema states, venous and arterial insufficiency, and pain caused by varicose veins or peripheral arterial occlusion.

EXAMPLES

The patients were given a full informed consent of the benefits and risks of the procedure. Due to the persistence of lower extremity pain refractory to all other treatments, the patients were determined to be candidates for a series of 5 nerve injections to the ankle followed by specific parameter electroanalgesia treatments utilizing the present wound therapy method. Without being limited by theory, it is anticipated that the nature of the interaction of the specific parameter electrical signaling with the local anesthetic will have additional beneficial effects on the spinal nerve, dorsal horn, and sympathetic chain, and therefore serve to improve any co-existing pathology.

After stable vital signs were recorded, the patients were placed in a seated position. Using sterile technique, the skin over ankle was prepped with a disinfectant (such as Betadine ×3, Purdue Products L.P. Stamford, Conn.), in the usual sterile manner. A mixture of 0.25% preservative free Marcaine was prepared in a sterile manner with a 5 cc syringe.

Areas of anesthetization completed for the procedure include a line along the anterior ankle. The deep Peroneal nerve was injected after passage of a 30 g 1-inch needle, with 2 cc of the solution being injected after aspiration. Then the superficial Peroneal nerve was injected with 1.5 cc solution, the Saphenous nerve was injected with 1.5 cc solution. the Sural nerve was injected with 1.5 cc solution, and the Posterior Tibial nerve was injected with 2 cc solution, in a like manner.

The patients tolerated the procedure well. The patients then underwent a 15-minute electro analgesia treatment using a high voltage (max. 440 V) and very low amperage (0.1-4.4 milliamps), AC output Neuromuscular Electrical Stimulator. The technology uses a biphasic pyramidal wave with a frequency of 47 Hz. Duty cycles are fixed at 1.5 seconds on and 1.8 seconds off There is no ramp time. These settings are preset with the intensity being the only variable.

A neuropathic pain assessment questionnaire was given to each patient prior to initiation of therapy and at the conclusion of therapy. The neuropathic pain assessment asks each patient to rank the perception of pain from 1 (little pain) to 10 (extreme pain). Before and after pictures were taken in each patient that presented with non-healing ulcers as well as those with significant impairment in local circulation. Patients were asked to return as directed for repeat treatments and follow up evaluation.

Example 1

Patient 1 was a 68 year old female with a past medical history of atrial fibrillation, diastolic congestive heart failure, hypertension, diabetes mellitus with associated chronic renal insufficiency and neuropathy, peripheral vascular disease, and dependent edema. Patient 1 complained of significant lower extremity parasthesia and pain and was referred for treatment with the present wound therapy method.

Upon physical examination of bilateral lower extremities the patient had significant gross edema to her mid thigh. The legs contained multiple Stage 1 ulcerations. Serous fluid weeped from the open wounds with erythematous changes consistent with peripheral venous disease. Pulses were palpable in both lower extremities. 10 g monofilament test was performed and was positive for the presence of diabetic neuropathy. Treatment was administered as described above. After two weeks of treatment, the skin in the affected lower extremity appeared visibly healed. FIG. 1 shows photographs of Patient 1 taken (a) at the early stages of treatment and (b) further into treatment, showing visibly healed skin.

Example 2

Patient 2 was a 76 year old male with a past medical history significant for peripheral vascular disease, hypertension, coronary artery disease, and tobacco use. Patient 2 complained of pain to a lower extremity. He was referred for vein ablation surgery but declined and was referred for treatment with the present wound therapy method. Physical examination of bilateral lower extremities revealed erythematous legs with absent peripheral pulses. Stage 1 to 2 ulcerations were seen measuring approximately 1×2 cm in diameter. Absence of blanching of the skin was noted indicating diminished vascular blood supply to the lower extremities. 10 g monofilament test was positive for the presence of peripheral vascular neuropathy. Treatment was administered as described above.

Figure 2:
FIG. 2 shows photographs of a taken (a) at the early stages of treatment and (b) after further treatment, showing skin in the affected lower extremity appearing much healthier.
Figure 2:
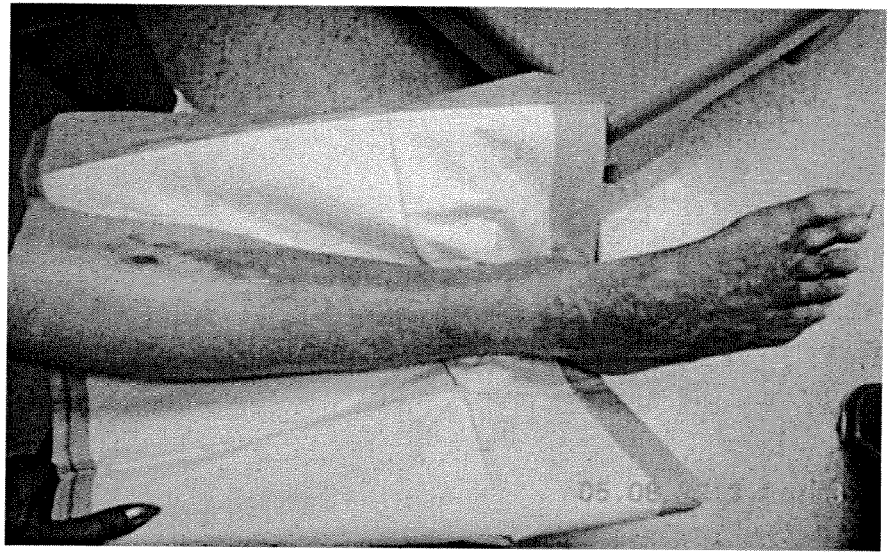

Treatment was initiated and revealed improved circulation verified by restitution of pedal pulses as well as complete healing of multiple wounds within 2 weeks of therapy. FIG. 2 shows (a) a photograph taken in the early stages treatment and (b) a photograph taken after further treatment, showing skin in the affected lower extremity appearing much healthier.

Example 3

Figure 3:
FIG. 3 shows photographs of a patient taken (a) at the early stages of treatment and (b) after further treatment, showing visible wound healing.
Figure 3:
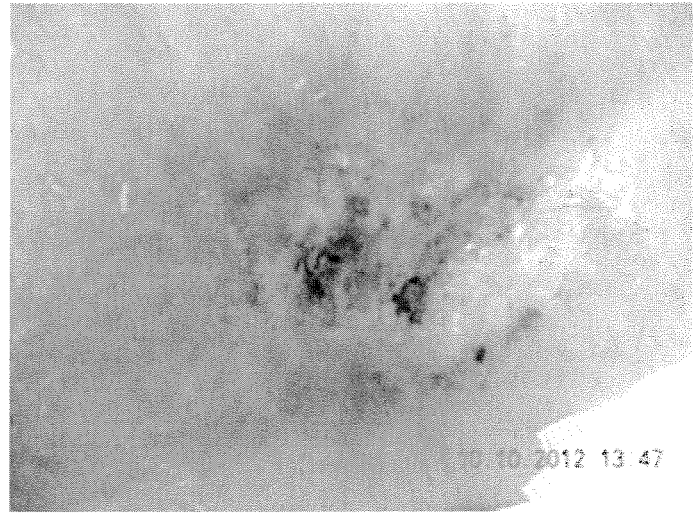
Figure 4:
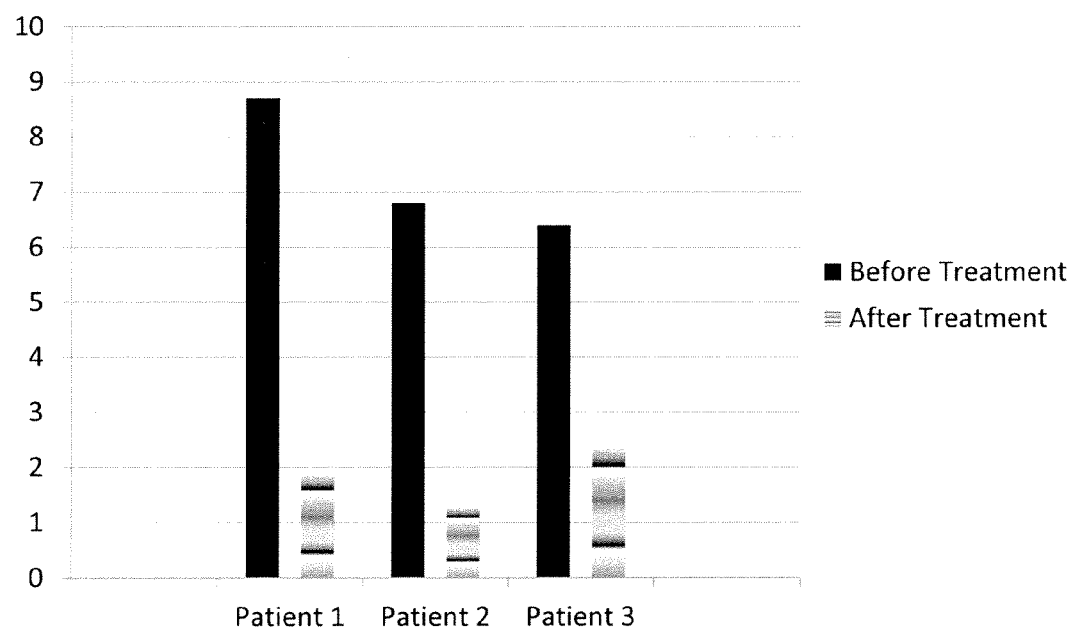
FIG. 4 shows a neuropathy pain scale comparison by patients before and after treatment with the wound therapy method.

Patient 3 was a 71 year old white female with a history of hypertension, hyperlipidemia, Waldenstrom macroglobulinemia, peripheral vascular disease, and prior below the knee amputation who was referred for the treatment of a stage four ulcer to the right medial upper thigh. She was discharged from the hospital two weeks prior, where she was admitted for wound debridement and IV antibiotic treatment. She had a history of previous wound infections and had undergone previous hyperbaric oxygen therapy. The medial thigh wound measured 6×8 cm in diameter and with gentle probing the underlying tendon was involved. This was a stage IV wound with significant wet gangrene and foul smelling odor in spite of chronic antibiotic therapy. The treatment was initiated and within the first few treatments, healthy granulation tissue began to form around the periphery. She had significant improvement with complete healing of the wound at day 30 of treatment. FIG. 3 shows (a) a photograph taken in the early stages of treatment and (b) a photograph taken further into treatment, showing a visibly healed wound.

Example 4

Patient 4 was a 62 year old male with history significant for ischemic cardiomyopathy hypertension peripheral vascular disease with significant and painful diabetic peripheral neurapothyy. He presented with stage 1 ulceration. Bilateral lower extremity examination was performed and indicated gross edema to mid thigh with significantly diminished peripheral pulses. The patient had stage 1 ulcerations to the lower tibial aspect of both legs with induration around the periphery, purulent discharge and foul odor. The wounds measured approximately 1×2 cm in diameter. Upon 10 g monofilament examination there was absent fine touch and proprioception indicating significant neuropathy. Treatment was initiated and within 10 treatments reevaluation of the wounds showed dry, well healed eschar with improved pain and sensation. These ulcerations remained healed and in follow up of over 1 year the patient has continued to show improvement.

Example 5

Additionally, four other patients were referred for evaluation and examination. All four patients presented with history of diabetic peripheral neuropathy with loss of protective sensation but did not have open persistent wounds. All four patients complained of neuropathic pain and exhibited classical signs of advanced tissue degradation as a result of their neuropathy. These patients were deemed to be at high risk for developing a diabetic foot ulcer and the decision was made to treat these patients with the same method described above as a preventative measure from the development of a lesion. Outcomes for these patients were consistent with results experienced by patients in the previous examples. All of the patients reported significant improvement in regards to pain, edema, circulation, walking distance, and quality of life.

REFERENCES

The following documents and publications are hereby incorporated by reference.

OTHER PUBLICATIONS

King H, Aubert R E, Herman W H. Global burden of diabetes, 1995-2025: prevalence, numerical estimates, and projections. *Diabetes Care.* 1998;21:1414-1431.

Boulton A J M, Kirsner R S, Vileikyte L. Clinical practice. Neuropathic diabetic foot ulcers. *N Engl J Med.* 2004;351: 48-55.

Boulton A J, Vileikyte L, Ragnarson-Tennvall G, Apelqvist J. The global burden of diabetic foot disease. *Lancet.* 2005; 366:1719-1724.

Apelqvist J, Larsson J. What is the most effective way to reduce incidence of amputation in the diabetic foot? *Diabetes Metab Res Rev.* 2000:16 (suppl 1):S75-S83.

Ramsey S D, Newton K, Blough D, et al. Incidence, outcomes, and cost of foot ulcers in patients with diabetes. *Diabetes Care.* 1999;22:382-387.

Sanders L J. Diabetes mellitus: prevention of amputation. *J Am Podiatry Med Assoc.* 1994;84:322-328.

Pecoraro R E, Reiber G E, Burgess E M. Pathways to diabetic limb amputation. Basis for prevention. *Diabetes Care.* 1990;13:513-521.

Moulik P K, Mtonga R, Gill G V. Amputation and mortality in new-onset diabetic foot ulcers stratified by etiology. *Diabetes Care.* 2003;26:491-494.

Margolis D J, Kantor J, Berlin JA. Healing of diabetic neuropathic foot ulcers receiving standard treatment. A meta-analysis. *Diabetes Care,* 1999; 22:692-695.

What is claimed is:

1. A method of improving wound healing and reducing pain in a patient having a peripheral wound, comprising:
    administering local injections of 0.25% bupivacaine hydrochloride in amounts from about 1 cc to about 2 cc at a plurality of nerve locations in proximity to the peripheral wound;
    placing electrical stimulator contact pads at a plurality of stimulation locations in proximity to the peripheral wound;
    performing electrostimulation through the contact pads for about fifteen minutes at a voltage of about 440 V and an amperage from about 0.1 to about 4.4 milliamps, wherein the electrostimulation utilizes a biphasic pyramidal wave with a frequency of about 47 Hz, wherein the electrostimulation is performed using duty cycles of about 1.5 seconds on and about 1.8 seconds off, and wherein the electrostimulation causes local and deep muscle contraction; and
    repeating the steps on the patient until an improvement in wound healing is achieved and the patient reports a decrease in pain.

2. The method of claim 1, wherein the plurality of nerve locations is about four or five nerve locations.

3. The method of claim 1, wherein the plurality of nerve locations includes the deep peroneal nerve, the superficial peroneal nerve, the saphenous nerve, the sural nerve, and the posterior tibial nerve.

4. The method of claim 1, wherein the plurality of nerve locations includes the Ilioinguinal nerve, the Genitofemoral nerve, the Obturator nerve, and the Anterior Cutaneous Femoral nerve.

5. The method of claim 1, wherein the plurality of stimulation locations is about four stimulation locations.

6. The method of claim 1, wherein the peripheral wound is located on a foot or lower leg of the patient.

7. The method of claim 1, wherein the peripheral wound is caused by diabetic foot ulcer, pressure ulcer, arterial ulcer, venous ulcer, peripheral vascular disease, chronic lymphedema, venous insufficiency, arterial insufficiency, varicose veins, or peripheral arterial occlusion.

* * * * *